United States Patent [19]

Lokken

[11] Patent Number: 4,611,992
[45] Date of Patent: Sep. 16, 1986

[54] SPRAY GUARD FOR DENTAL TOOL

[76] Inventor: Oddvin Lokken, 131 Forest Ave., Rye, N.Y. 10580

[21] Appl. No.: 667,549

[22] Filed: Nov. 2, 1984

[51] Int. Cl.$^4$ ................................................ A61C 1/16
[52] U.S. Cl. ..................................... 433/116; 433/29; 433/80; 128/62 A
[58] Field of Search ..................... 433/116, 88, 87, 80, 433/82, 86, 29, 136, 139; 128/66, 62 A

[56] References Cited

U.S. PATENT DOCUMENTS

| | | | |
|---|---|---|---|
| 465,716 | 12/1891 | Meister | 433/139 |
| 663,178 | 12/1900 | Kuns | 433/136 |
| 1,122,086 | 12/1914 | Dunlop | 433/29 |
| 1,954,623 | 4/1934 | Gross | 433/87 |
| 2,092,549 | 9/1937 | Craigo | 433/136 |
| 2,637,107 | 5/1953 | Daigle | 433/136 |
| 2,680,908 | 6/1954 | Daigle | 433/136 |
| 2,731,722 | 1/1956 | Wilen | 433/116 |
| 2,835,084 | 5/1958 | Fotre | 433/116 |
| 3,401,690 | 9/1968 | Martin | 128/62 A |
| 3,421,222 | 1/1969 | Newman | 433/36 |
| 4,368,040 | 1/1983 | Weissman | 433/36 |
| 4,382,785 | 5/1983 | Lococo | 433/36 |
| 4,424,036 | 1/1984 | Lokken | 433/116 |

Primary Examiner—John J. Wilson
Attorney, Agent, or Firm—Jacobs and Jacobs

[57] ABSTRACT

An anti-splash device for attachment to a dental tool that delivers an aqueous fluid from a nozzle, which comprises an inverted U-shaped member having a base and integral, opposed legs depending therefrom, one of said legs having a bore extending therethrough and operable to secure said member to the nozzle of said dental tool, said bore providing access to the space between said opposed legs.

8 Claims, 8 Drawing Figures

SPRAY GUARD FOR DENTAL TOOL

The present invention relates to an accessory for a dental tool, and more particularly to a device for confining to the patient's mouth the splashing of water and other aqueous fluids encountered during dental prophylaxis.

It is well known that there is considerable splashing of water and debris during dental prophylaxis using ultrasonic and/or jet air-polishing dental prophylaxis tools. In ultrasonic dental prophylaxis tools, water is delivered with ultrasonic oscillation to remove calculus deposits from the teeth. The jet air-polishing dental tool delivers a stream of air and water containing a dental prophylaxis cleaning powder, such as sodium bicarbonate and calcium sulfate, for removing stains and/or plaque from exposed surfaces of tooth enamel. Ultrasonic dental prophylaxis tools and air-polishing dental prophylaxis tools are commercially available, for example, CooperCare Inc. of Palo Alto, Calif. manufactures a dental prophylaxis unit capable of functioning in both an ultrasonic mode and an air-polishing mode.

Despite care exercised by the dentist or dental hygienist, the splashing encountered during the dental prophylaxis often sprays the gown, face, hair and glasses of the dentist or hygienist, and sometimes the patient's garments as well.

In recognition of this problem, the patient and the dentist and/or hygienist is usually extensively draped to prevent soiling of clothing. The dentist's office and equipment is regularly inspected and cleaned after the dental prophylaxis has been completed.

Dental isolators have been proposed for use with air abrasive techniques and other dental prophylaxis treatments, such as proposed in U.S. Pat. Nos. 2,637,107 and 2,680,908 of B. J. Daigle, but such devices are unduly cumbersome and are unduly difficult to use. Neither lends itself to providing a disposable anti/splash device.

Various dental dams have been proposed, such as those in Kuns, U.S. Pat. No. 663,178 and Craigo, U.S. Pat. No. 2,092,549, but these merely isolate the tooth being treated and do not provide protection to the dentist, hygienist or the patient.

Attachment to dental tools have likewise been provided, such as proposed in Wilen, U.S. Pat. No. 2,731,722 and my U.S. Pat. No. 4,424,036. However, these dental attachments do not provide the degree of protection afforded by my new invention.

The present invention now provides an anti-splash device for attachment to a dental tool that delivers an aqueous fluid from a nozzle, which comprises an inverted U-shaped member having a base and integral opposed legs depending from the base. One of the legs has a bore extending therethrough, which is operable to secure the U-shaped member to the nozzle of the dental tool. The bore also provides access to the space between the opposed legs of the U-shaped member.

In use, the U-shaped member of my invention is attached to the nozzle of the dental tool and is placed over the tooth being treated, with the tooth being within the space between the two legs. The leg closest to the dentist acts as a barrier to prevent the material from splashing out of the patient's mouth. The other leg acts to confine the aqueous fluid and other material to within the small space between the legs and thus prevent this material from spraying into the patient's mouth where it could damage the tongue and/or roof of the mouth. For example, when the tool is used to spray between the teeth, the fluid passes through the teeth and into the rest of the mouth.

The anti-splash device according to the present invention also finds utility when the dental tool is used to clean the rear of the teeth. In this case, the tool is pointing towards the dentist or hygienist and the anti-splash device according to the present invention provides a barrier to prevent fluid from escaping the mouth and striking the dentist or hygienist.

The present invention is illustrated in terms of its preferred embodiment in the accompanying drawing, in which like reference numerals denote like parts. Reference is made to the accompanying drawing in which.

Figure 1:
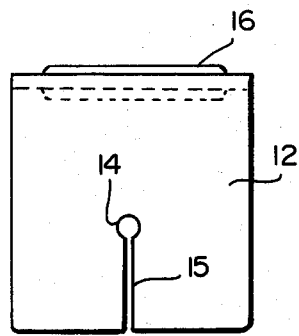
FIG. 1 is a front elevational view of the anti-splash device according to the present invention.
Figure 2:
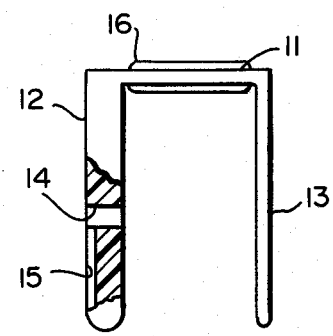
FIG. 2 is a side elevational view, partly in section, of the anti-splash device.
Figure 3:
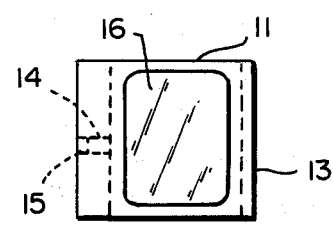
FIG. 3 is a top plan view of the anti-splash device.

Referring to the drawings, FIGS. 1–3 show an anti-splash device 10, which is in the form of an inverted U having a base 11 and depending legs 12 and 13. Preferably, the base 11 and depending legs 12, 13 are integral, but they can be separate elements connected together.

Leg 12 has an exposed, planar exterior face having bore 14 therethrough and a groove 15 therein extending from the free-end of the leg 12 to the bore 14. Bore 14 provides access to the space between the opposed legs 12, 13 and is operable to secure the device 10 to a dental tool as shown in FIG. 4.

Lens 16 is a magnifying lens so that the practicioner may obtain a better view of the procedure. Device 10 may be made of transparent plastic, in which case lens 11a may be integral with the base 11 when device 10 is formed, such as by molding. Device 10 may also be of rubber or non-transparent plastic, in which case lens 11a is secured to base 11 as by a non-toxic adhesive.

Figure 4:
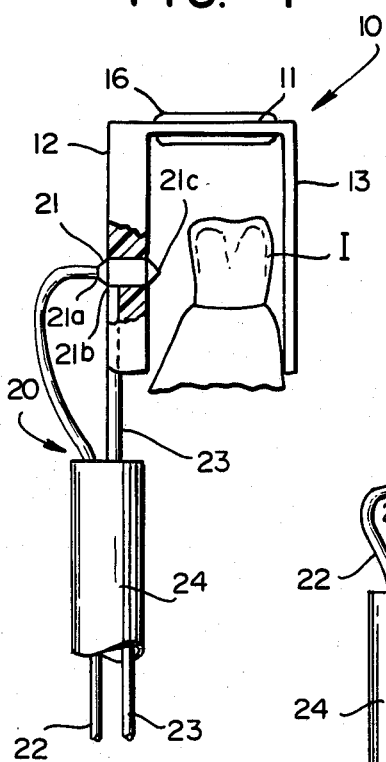
FIG. 4 is a diagrammatic view showing the anti-splash device attached to an air polishing dental prophylaxis unit.

FIG. 4 illustrates the device 10 secured to an air-polishing tool 20. The air-polishing tool 20 includes a nozzle 21 having an inlet 21a at its rear end (as viewed in FIG. 4) and another inlet 21b at its bottom side. Connected to inlet 21a is conduit 22, which carries a mixture of air and a dental cleaning powder such as sodium bicarbonate. Connected to inlet 21b is conduit 23, which carries water. Conduits 22 and 23 pass through the handle 24 to suitable supply means (not shown). In operation, the dental tool 20 delivers an aqueous fluid comprising water, air and the dental cleaning powder from outlet nozzle 21c onto the exposed surface of the tooth T. When the tool 20 is used to treat the front surface of the tooth, leg 12 will be facing the dentist or hygienist and will prevent materials from leaving the mouth and striking the operator. In this position, leg 13 will protect the rest of the mouth from coming into contact with the aqueous fluid delivered by tool 20, such as when the tool is used to clean the space between adjacent teeth. When the tool 20 is used to treat the rear surface of the tooth, then the leg 13 will protect the operator and leg 12 will protect the interior of the mouth.

Figures 5, 6:
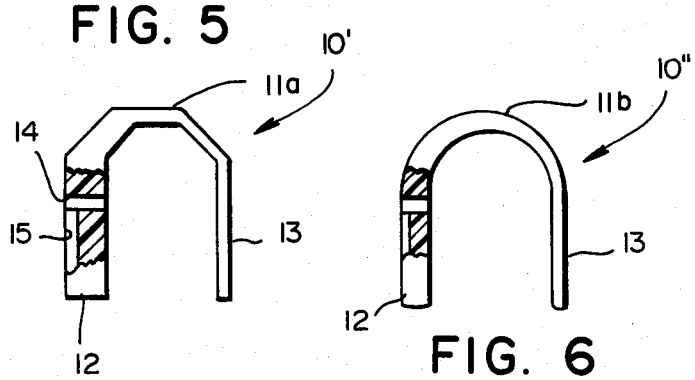
FIGS. 5 and 6 are side elevational views, partly in section, of alternative embodiments of the present invention.

FIGS. 5 and 6 show modifications 10' and 10" of the anti-splash device 10, in which the planar base 11 is replaced by a polygonal base 11a and by a curved base 11b, respectively. In the embodiment shown in FIGS. 1–4, the anti-splash device includes a groove 15 that lies in the exposed, exterior face of the leg 12. This groove 15 accommodates the air conduit 23. The groove 15 and conduit 23 together lock the anti-splash device in place and prevent rotation of the anti-splash device with respect to the nozzle 21.

Figures 7, 8:
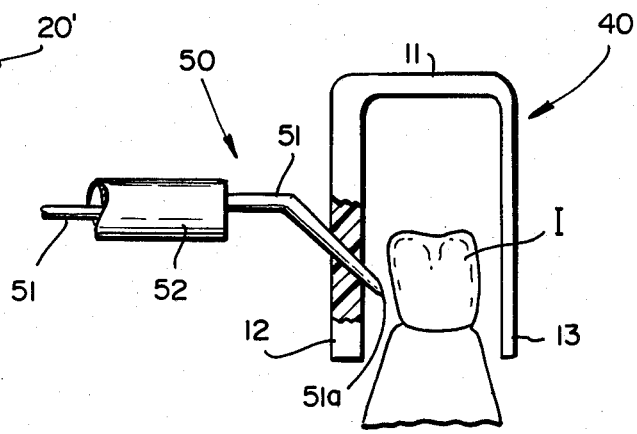
FIG. 7 is a view similar to FIG. 4, showing an anti-splash device according to the present invention secured to a different air-polishing dental prophylaxis tool.
FIG. 8 is a view similar to FIG. 4 showing an anti-splash device according to the invention secured to an ultrasonic dental prophylaxis tool.

FIG. 7 illustrates another embodiment of the invention in which the air-polishing tool 20' has an offset conduit 23'. In this case, the anti-splash device 30 does not include any groove lying in the exterior face of leg 12, and the anti-splash device 30 is secured to the tool 20' by means of the bore 14.

In FIGS. 1–7, the bore 14 is preferably perpendicular to the plane containing the leg 12, but in FIG. 8, the dental tool 50 is used with a splash guard 40 that has a bore 14' that extends through the leg 12 at an angle other than 90° with respect to the plane containing the leg 12. Tool 50 may be, for example, an ultrasonic dental prophylaxis tool that delivers water with ultrasonic oscillation through the conduit 51 and the nozzle 51a formed at the end thereof. The legs 12 and 13 of the anti-splash device 40 will protect the dentist and the interior of the patient's mouth when the tool 50 is used to treat the front or rear surfaces of the teeth. As is known, the conduit 51 passes through the handle 52 to a suitable source of supply.

I claim:

1. A dental tool for delivery of an aqueous fluid to teeth, comprising an elongated nozzle provided with an aqueous fluid inlet at one end and an aqueous fluid outlet at the other end, and an inverted U-shaped member having a base and integral, opposed legs depending therefrom, one of said legs having a bore extending therethrough, said nozzle being removably inserted in said bore with said nozzle outlet facing said other leg, whereby when the U-shaped member is placed over a tooth being treated, the leg closest to the operator of the tool acts to prevent material from splashing out of the patient's mouth.

2. Apparatus according to claim 1, wherein said member is made of transparent flexible plastic.

3. Apparatus according to claim 1, wherein said base has a magnifying lens means for viewing said space.

4. A dental tool comprising an elongated nozzle having outlet means at one end and inlet means at the other end and at one side thereof, first conduit means connected to said inlet means at said side and extending transversely away from said nozzle, second conduit means connected to said inlet means at said other end, and an inverted U-shaped member having a base and integral opposed legs depending therefrom, one of said legs having a bore extending therethrough and a groove lying in the exterior face of said leg and extending from the free end of said leg to said bore, said nozzle being removably inserted in said bore with said nozzle outlet facing said other leg and said first conduit means being removably inserted in said groove, whereby said U-shaped member is removably secured to said nozzle and said first conduit means.

5. Apparatus according to claim 4, wherein said groove is perpendicular to said bore and said bore is perpendicular to said exterior face.

6. Apparatus according to claim 5, wherein said member is made of transparent flexible plastic.

7. Apparatus according to claim 4, wherein said first conduit is operable to deliver water to said nozzle and said second conduit is operable to deliver a mixture of air and a dental cleaning powder to said nozzle.

8. Apparatus according to claim 4, wherein said base has a magnifying lens means for viewing said space.

* * * * *